US011013884B2

(12) United States Patent
Russin, Sr. et al.

(10) Patent No.: US 11,013,884 B2
(45) Date of Patent: May 25, 2021

(54) WEIGHTED BLANKET

(71) Applicant: Sherwood Industries Inc., Niles, IL (US)

(72) Inventors: Robert T. Russin, Sr., Chicago, IL (US); Robert T. Russin, Jr., Des Plaines, IL (US); Carole L. Studenroth, Glenview, IL (US); Annette L. Ashbacher, Vernon Hills, IL (US); Timothy W. Russin, Des Plaines, IL (US); Christopher T. Marras, Chicago, IL (US); Susan R. Barr, Mount Prospect, IL (US); Joseph W. Marras, Arlington Heights, IL (US)

(73) Assignee: Sherwood Industries Inc., Niles, IL (US)

( * ) Notice: Subject to any disclaimer, the term of this patent is extended or adjusted under 35 U.S.C. 154(b) by 390 days.

(21) Appl. No.: 16/212,394

(22) Filed: Dec. 6, 2018

(65) Prior Publication Data

US 2020/0179641 A1  Jun. 11, 2020

(51) Int. Cl.
*A61M 21/02* (2006.01)
*A47G 9/02* (2006.01)
*A61M 21/00* (2006.01)

(52) U.S. Cl.
CPC .......... *A61M 21/02* (2013.01); *A47G 9/0207* (2013.01); *A47G 9/0223* (2013.01); *A47G 9/02* (2013.01); *A61M 2021/0022* (2013.01)

(58) Field of Classification Search
CPC ..... A61M 21/02; A61M 21/00; A47G 9/0223; A47G 9/0207; A47G 9/0215; A47G 9/02; A47G 9/00

USPC .................... 5/502, 500, 499, 482
See application file for complete search history.

(56) References Cited

U.S. PATENT DOCUMENTS

| 2,494,664 | A | 1/1950 | Lubow |
| 6,674,087 | B2 | 1/2004 | Cadwalader |
| 7,870,623 | B2* | 1/2011 | Judd ................. A61H 7/001 5/502 |
| 9,901,197 | B2 | 2/2018 | Lucas et al. |
| 10,617,158 | B2* | 4/2020 | Pacheco ............ A61M 21/02 |
| 2009/0100568 | A1* | 4/2009 | Judd ................. A61H 7/001 2/95 |
| 2011/0163248 | A1 | 7/2011 | Beck |
| 2017/0196381 | A1 | 7/2017 | Lucas et al. |
| 2018/0000171 | A1* | 1/2018 | Pacheco ............ A41D 31/02 |
| 2019/0274454 | A1* | 9/2019 | Bidhendi .......... A47G 9/0223 |
| 2020/0179641 | A1* | 6/2020 | Russin, Sr. ........ B32B 27/304 |

(Continued)

FOREIGN PATENT DOCUMENTS

| CA | 3020129 A1 * | 12/2018 | ......... A47G 9/0223 |
| CN | 108 784 193 A | 11/2018 | |

(Continued)

OTHER PUBLICATIONS

Jun. 30, 2020—ISR & WO—App. No. PCT/US19/62844.

*Primary Examiner* — Robert G Santos
(74) *Attorney, Agent, or Firm* — Banner & Witcoff, Ltd.

(57) ABSTRACT

A weighted blanket with outer fabric layers and an inner layer comprising a continuous sheet of material may be formed from a core material comprising a polymer material and a filler material. The inner layer may include a plurality of ventilation apertures spaced that extend through the inner layer or may be a solid sheet.

20 Claims, 5 Drawing Sheets

(56) References Cited

U.S. PATENT DOCUMENTS

2020/0196685 A1* 6/2020 Williams .................. A47G 9/04
2020/0238045 A1* 7/2020 Pacheco ................ A61M 21/00
2020/0405079 A1* 12/2020 Bidhendi ............... A45C 13/10

FOREIGN PATENT DOCUMENTS

| WO | WO-2019177770 A1 * | 9/2019 | ........... A47G 9/0261 |
| WO | WO-2020117499 A2 * | 6/2020 | ............. B32B 25/10 |
| WO | WO-2020117499 A3 * | 8/2020 | ............... B32B 7/05 |

* cited by examiner

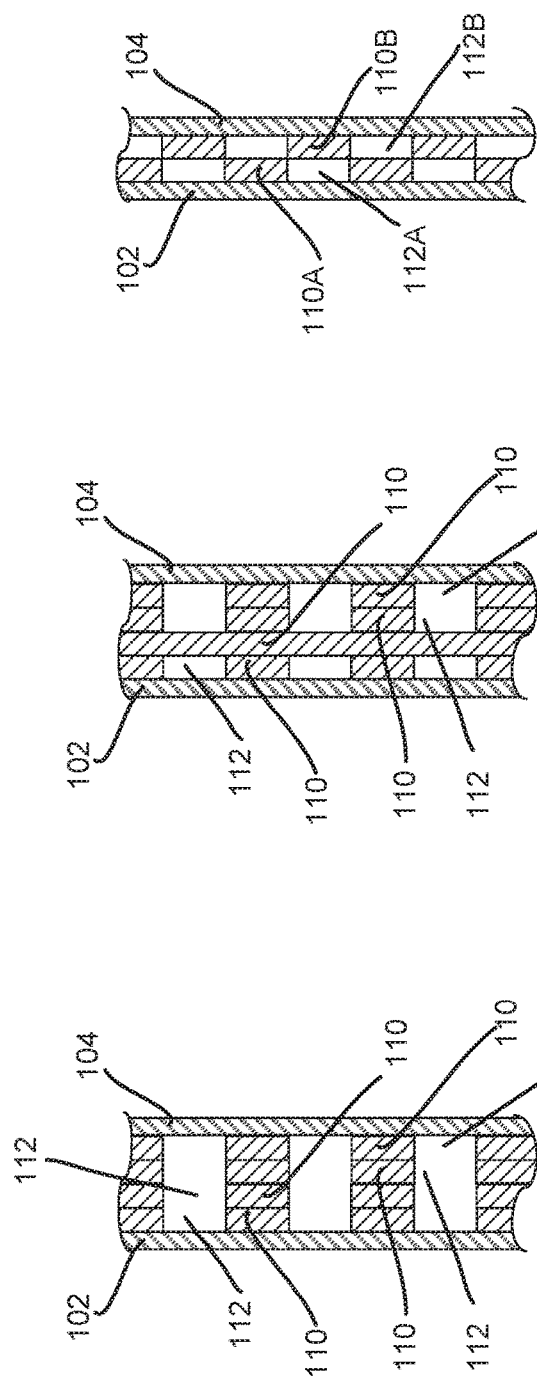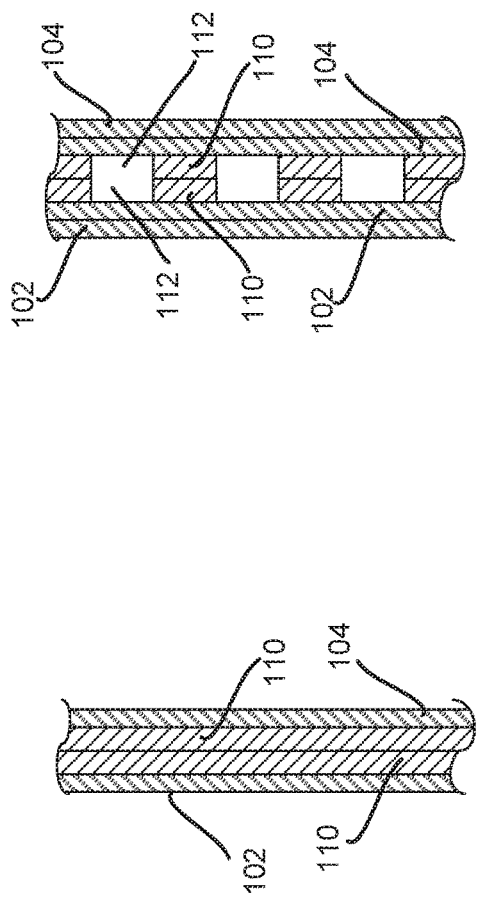

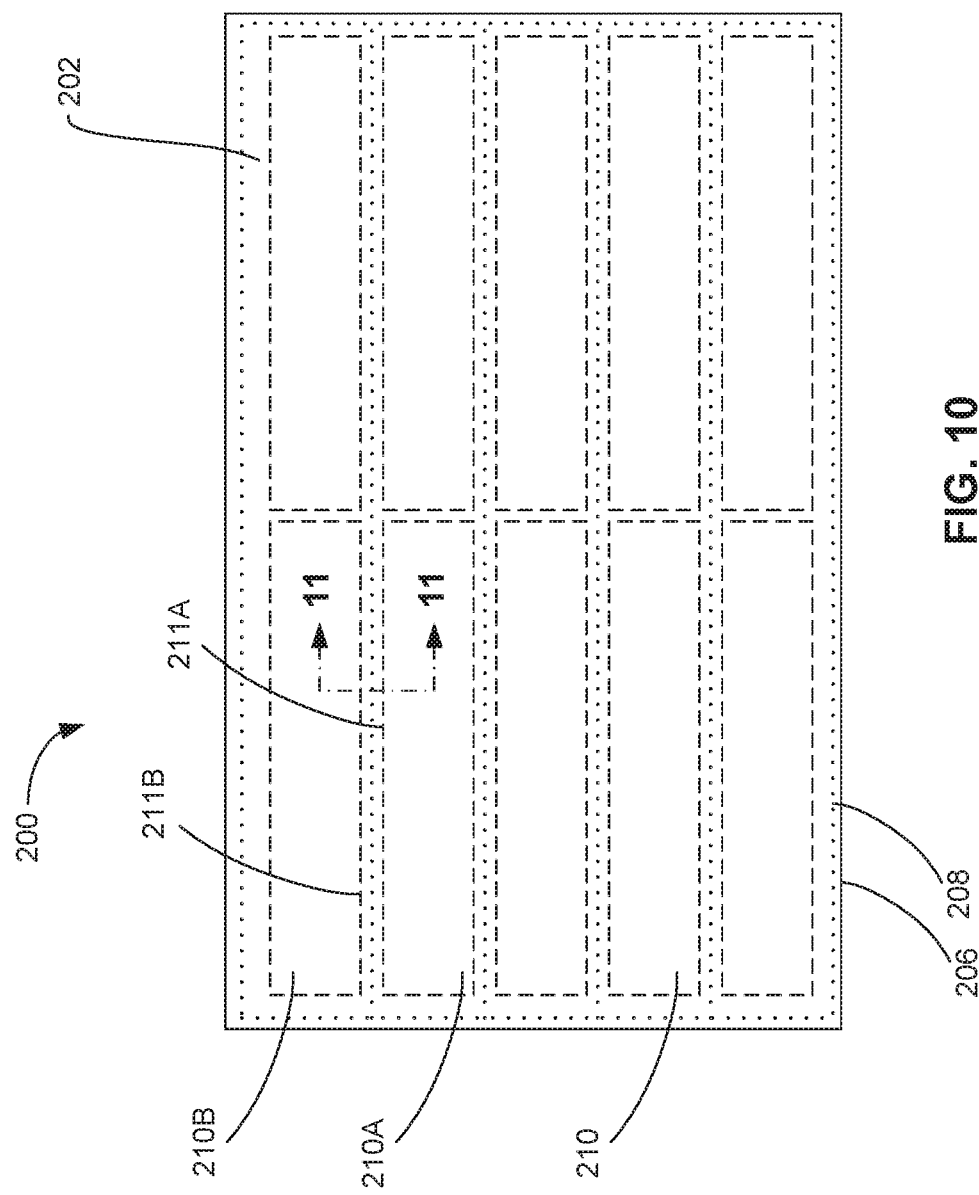
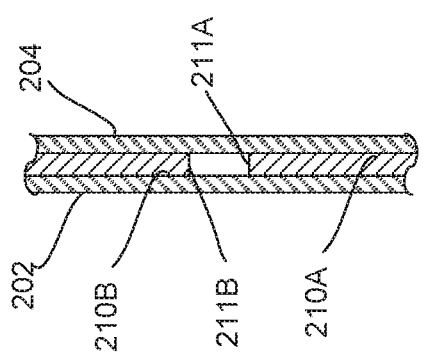

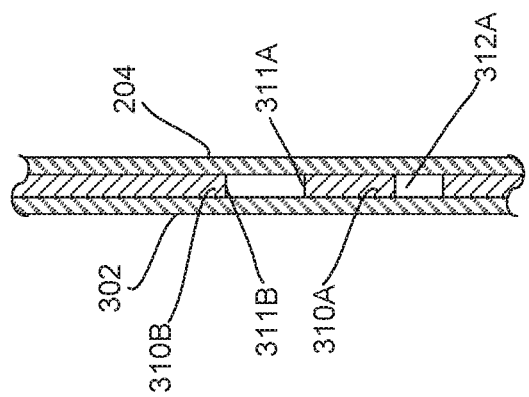
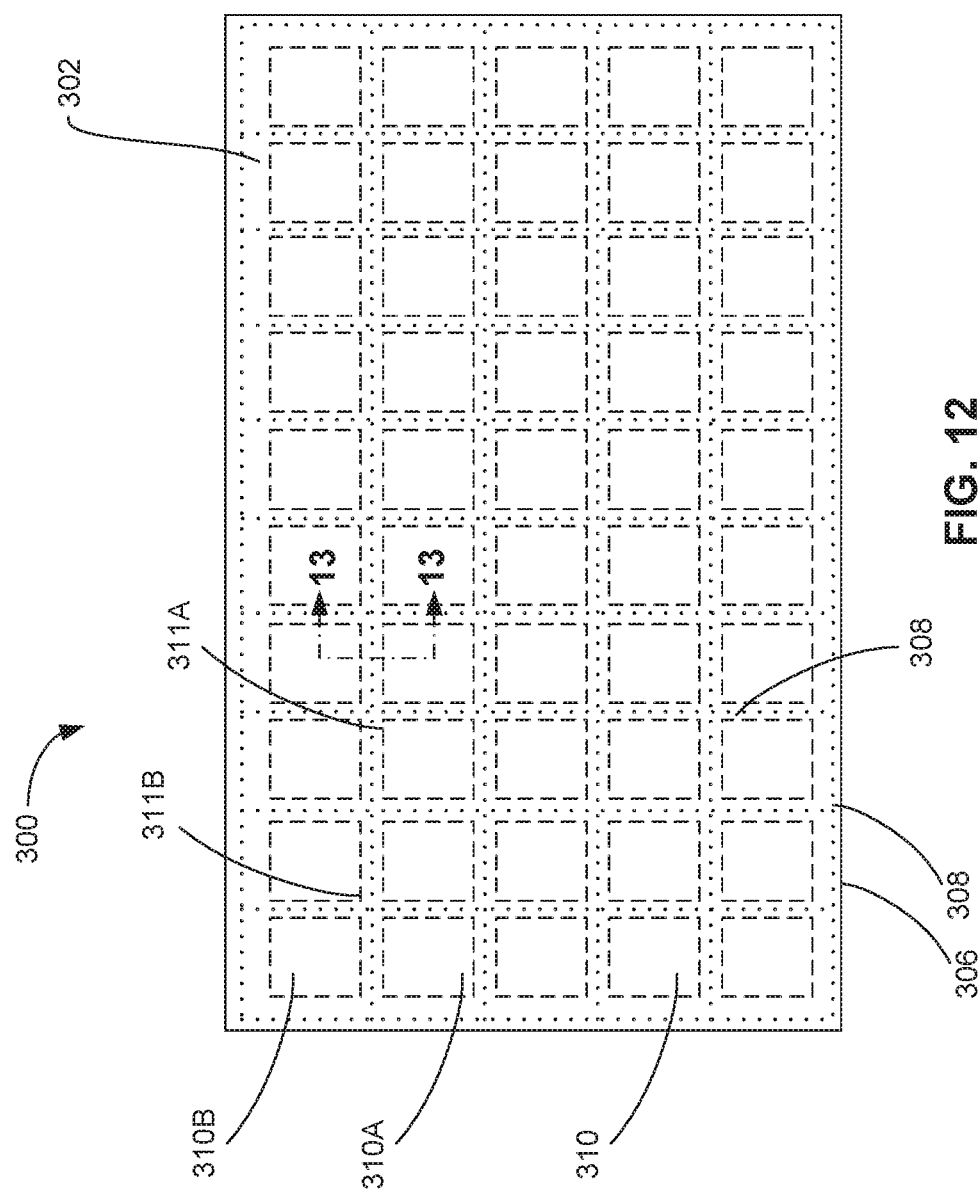

WEIGHTED BLANKET

FIELD OF THE INVENTION

This disclosure relates to a weighted blanket.

BACKGROUND

Many weighted blankets use plastic, glass, or metal pellets/beads that are sewn or quilted into squares or pockets in a blanket to provide the weight. This method of weighting can create a blanket that has an unevenly weighted feel, is noisy as the pellets/beads move around, or is rough to the touch as the beads can be felt through the fabric. All of these factors can make the blanket uncomfortable, which can lead to reduced usage.

BRIEF SUMMARY

This disclosure may relate to a blanket comprising: a top layer comprising a first fabric material, a bottom layer comprising a second fabric material, and an inner layer positioned between the top layer and the bottom layer, where the inner layer is a continuous sheet of a core material. The core material may include a base polymer material and a filler material, where the core material has a density between 0.6 grams per cubic centimeter and 10 grams per cubic centimeter or where the core material has a density between 1.4 grams per cubic centimeter and 3.2 grams per cubic centimeter. The top layer, the bottom layer, and the inner layer may be joined together using a central stitch located in a central region of the blanket, where the central region is defined as an area spaced a distance of at least thirty percent of a total width of the blanket. The inner layer may have a thickness between 0.001 inches and 0.25 inches, and the inner layer may be a solid sheet or have a plurality of ventilation apertures extending through the inner layer. In addition, the continuous sheet of core material may have length that is at least 60 percent of a total length of the blanket. The base polymer material may be one of a group consisting of: an ethylene vinyl acetate, a thermoplastic elastomer, a thermoplastic olefin, a thermoplastic vulcanizate, a styrenic block copolymer, a styrene ethylene butylene styrene, a thermoplastic rubber, a polyvinyl chloride, a polyurethane, a polyethylene, a polyethylene terephthalate, a polypropylene, a polyolefin, a thermoplastic, a foam, a thermoset plastic, a cured rubber, a silicone, a functionalized polymer, and a thermoplastic blend, and the filler material may be one of a group consisting of: a mineral, a sulfate, an oxide, a hydroxide, a sulfide, a carbonate, a phosphate, a halide, a silicate, a glass, or alloys such as leaded glass, a fabric material, or a different polymer with a higher density than the base polymer material, or other non-metallic material. As one option, the filler material may be a non-toxic and/or a metallic material.

Other aspects of this disclosure may relate to a blanket comprising: a top layer formed from a sheet of a first fabric material, a bottom layer formed from a second fabric material, and a plurality of inner layers positioned between the top layer and the bottom layer, where each inner layer of the plurality of inner layers may be a continuous sheet of a core material. The core material may include a base polymer material and a filler material, where the filler material may have a higher density than the base polymer material, and a first inner layer of the plurality of inner layers may be spaced apart from and arranged next to a second inner layer of the plurality of inner layers such that a first perimeter edge of the first inner layer is spaced a minimum distance from a first perimeter edge of a second inner layer of the plurality of inner layers, where the minimum distance between the first perimeter edge of the first inner layer and the first perimeter edge of the second inner layer is within a range of 0.25 inches and 2 inches. The inner layer may have a plurality of ventilation apertures extending through the inner layer, where a largest distance across each ventilation aperture of the plurality of ventilation apertures is between 0.125 inches and 2.5 inches. Optionally, at least one of the plurality of ventilation apertures have a circular shape, where at least one circular shaped ventilation aperture have a diameter between 0.125 inches and 2.5 inches.

Yet other aspects of this disclosure may relate to a blanket comprising: a top layer comprising a first fabric material, a bottom layer comprising a second fabric material, and an inner layer positioned between the top layer and the bottom layer, where the inner layer is a continuous sheet of a core material and the core material includes a base polymer material and a filler material. The filler material may have a density that is greater than a density of the base polymer material such that a density of the core material is within a range of between 0.6 grams per cubic centimeter and 10 grams per cubic centimeter. The inner layer may have a plurality of ventilation apertures extending through the inner layer and also have a durometer between 1 Shore A and 87 Shore A, when measured according to American Standard of Testing and Materials (ASTM) D2240 titled "Standard Test Method for Rubber Property—Durometer Hardness." Optionally, the blanket may have an inner layer that comprises a plurality of inner layers, where a first inner layer of the plurality of inner layers is positioned adjacent and above a second inner layer of the plurality of inner layers.

BRIEF DESCRIPTION OF THE DRAWINGS

FIG. 5 is an enlarged partial cross-section view of an alternative embodiment of the weighted blanket of FIG. 1;

FIG. 6 is an enlarged partial cross-section view of an alternative embodiment of the weighted blanket of FIG. 1;

FIG. 7 is an enlarged partial cross-section view of an alternative embodiment of the weighted blanket of FIG. 1;

FIG. 8 is an enlarged partial cross-section view of an alternative embodiment of the weighted blanket of FIG. 1;

FIG. 9 is an enlarged partial cross-section view of an alternative embodiment of the weighted blanket of FIG. 1;

FIG. 10 is a top view of an alternate embodiment of the weighted blanket as disclosed herein; and FIG. 11 is an enlarged partial cross-section view of the weighted blanket of FIG. 10 as disclosed herein.

FIG. 12 is a top view of an alternate embodiment of the weighted blanket as disclosed herein; and FIG. 13 is an enlarged partial cross-section view of the weighted blanket of FIG. 12 as disclosed herein.

DETAILED DESCRIPTION

In the following description of various example structures according to the invention, reference is made to the accompanying drawings, which form a part hereof, and in which are shown by way of illustration various example devices, systems, and environments in which aspects of the invention may be practiced. It is to be understood that other specific arrangements of parts, example devices, systems, and environments may be utilized and structural and functional modifications may be made without departing from the scope of the present invention.

Also, while the terms "top," "bottom," "front," "back," "side," "rear," and the like may be used in this specification to describe various example features and elements of the invention, these terms are used herein as a matter of convenience, e.g., based on the example orientations shown in the figures or the orientation during typical use. "Plurality" may be used to define a quantity greater than one. Nothing in this specification should be construed as requiring a specific three dimensional orientation of structures in order to fall within the scope of this invention. The reader is advised that the attached drawings are not necessarily drawn to scale.

Figure 2:
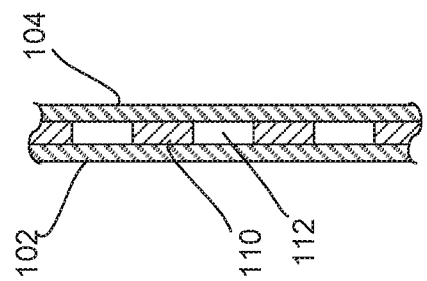
FIG. 2 is an enlarged partial cross-section view of the weighted blanket of FIG. 1 as disclosed herein.
Figure 1:
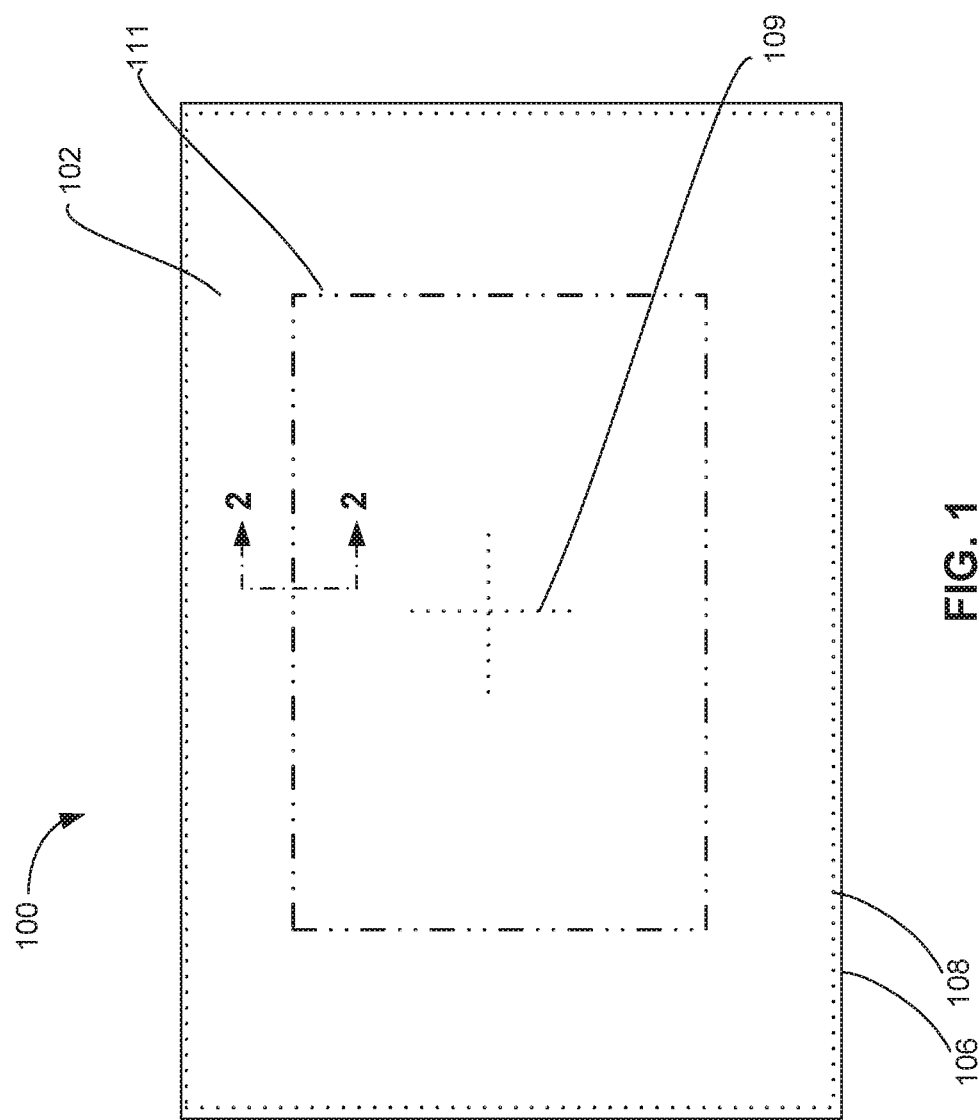
FIG. 1 is a top view of a weighted blanket as disclosed herein.

Generally, this disclosure relates to a weighted blanket 100 having a top layer 102, a bottom layer 104, and an inner layer 110 positioned between the top layer 102 and the bottom layer 104 as shown in FIGS. 1 and 2. The blanket 100 may have exterior or perimeter edges 106 that extend around the perimeter of the blanket 100. The top layer 102, bottom layer 104, and inner layer 110 may be sewn together by stitching 108 as known to one skilled in the art. The stitching 108 may be arranged around the perimeter and/or in a quilted pattern, or other pattern known to one skilled in the art. In addition, the top layer 102, the bottom layer 104, and the inner layer 110 may be joined together using a central stitch or stitching 109 located in a central region 111 of the blanket 100 where the stitching 109 passes through the top, bottom, and inner layers 102, 104, 110. The central region 111 may be defined as a region of the blanket spaced a distance from the perimeter edges 106 where the distance from the perimeter edges is at least thirty percent of a total width of the blanket 100. The central stitching 109 may help to secure the inner layer 110 to the outer layers 102, 104 such that the layers 102, 104, 110 move together. The central stitching 109 may be in a single line of stitching, or a pair of lines of stitching that cross each other. Additionally, the central stitching 109 may be generally parallel to the perimeter edges 106, or the central stitching 109 may be oriented at an oblique angle to the perimeter edges 106. The inner layer 110 may be a continuous sheet that extends as a unitary sheet that helps to provide an evenly weighted, comfortable, and quiet blanket.

While the blanket shown in the exemplary embodiment illustrated in FIG. 1 is rectangular in shape, the blanket 100 may have any shape such as square, circular, or any geometric shape. In addition, the blanket may have any size and may have an overall weight of 0.5 pounds and 60 pounds. The blanket 100 may be sized according to the desired usage but not limited to exemplary embodiments of a throw, a towel, an afghan, a blanket, a sheet, a comforter, a duvet cover, a wrap, a body wrap, a partial body part wrap (i.e. a neck wrap), an article of apparel (i.e. a weighted vest), a beach blanket, a therapy pad, a therapy blanket that may be used indoors or outdoors, such as in a user's home, a doctor's office, a school, a nursing home, or other institution where the calming effect of a weighted blanket would be helpful.

The inner layer 110 may be a continuous solid sheet of material that is free of any ventilation apertures or a continuous sheet with a plurality of ventilation apertures 112, where the material is a core material of a base polymer material and a filler material. As defined herein, the stitching 108, 109 may form small openings within the layers 102, 104, 110, but the openings formed by the stitching 108, 109 do not constitute ventilation apertures 112 as described herein. The core material may comprise a varied amount of filler material depending on the desired characteristics for the inner layer 110. For example, the filler material may be within a range of 70 percent to 85 percent when measured as a percentage by volume of the core material, or the filler material may be within a range of 50 percent to 90 percent, or within a range of 20 percent to 90 percent, or within a range of 5 percent to 99.9 percent when measured as a percentage by volume of the core material. The density, or specific gravity, of the filler material may be higher than the density of the base polymer material. Thus, as the percentage of filler material increases, the density of the core material may increase such that the core material forming the inner layer may have a density within a range of 1.8 grams per cubic centimeter (g/cc) and 3.2 g/cc, or within a range 1.5 g/cc and 6 g/cc, or within a range of 1.2 g/cc and 8 g/cc, or within a range of 0.6 g/cc and 10 g/cc. In addition, as the percentage of filler material increases, the stiffness and hardness of the core material may increase. The durometer of the core material may preferably be within a range of 15 Shore A to 30 Shore A, or within a range of 10 Shore A to 50 Shore A, or within a range of 1 Shore A to 87 Shore A. The durometer may be measured according to ASTM D2240 titled "Standard Test Method for Rubber Property—Durometer Hardness."

The base polymer material may be a polymer that can deliver adequate flexibility as to not inhibit the movement of the fabric or create any discomfort for the user. For example, the base polymer material may be one of a variety of polymers, such as a styrenic block copolymer (SBC), a styrene ethylene butylene styrene (SEBS), an ethylene vinyl acetate (EVA), a thermoplastic elastomers (TPE), thermoplastic olefin (TPO), thermoplastic vulcanizates (TPV), a thermoplastic rubber (TPR), a polyvinyl chloride (PVC), a polyurethane (PUR), a polyethylene (PE), polyethylene terephthalate (PET), polypropylene (PP), a thermoplastic urethane (TPU), a polyolefin, a thermoplastic, a foam, a thermo-set plastic, a cured rubber, a silicone, a functionalized polymer, a thermoplastic blend, or other polymer blend. The base polymer material may have a density within a range of 0.80 g/cc and 1.6 g/cc, or may have a density within a range of 0.6 g/cc and 2.5 g/cc. As another option, the base polymer material may be a virgin polymer or may include a recycled amount of polymer.

The filler material may be one of a variety of materials that are non-toxic and safe for use with people and animals. Preferably, the filler material may have a higher density than the density of the base polymer material and be encapsulated and dispersed evenly within the polymer material. For example, the filler material may have a density within a range of 2.5 g/cc and 10 g/cc, or within a range of 1.5 g/cc and 15 g/cc. The filler material may be a powder or small particle that is mixed with the base polymer material when the base polymer material is in pellet form to create a core material mixture. The core material mixture may then be melted and formed into a continuous sheet of the core material. The continuous sheet of filled polymer material may be formed as an extruded sheet, cast sheet, a calendared sheet, a vulcanized sheet, a liquid cured sheet, or blown film sheet. As an alternative, the core material may be formed using a solvent casting method, where the base polymer material is dissolved in a solvent and then mixed with the filler material while in a liquid form. For example, the filler material may be a non-metallic material such as a mineral, such as calcium carbonate and talc, a sulfate (e.g., such as barium sulfate), an oxide, a hydroxide, a sulfide, a carbonate, a phosphate, a halide, a silicate, a glass (e.g, such as glass beads, leaded glass, or types of silicate glass), diametric (diatomaceous) earth, a fabric material, or a different polymer with a higher density than the base polymer material, or other non-metallic material. As another option, the filler material may be a metallic material, such as an atomized metal, a powdered metal, a metallic oxides, a clay, or an ore. Examples of metallic materials may be iron, copper, tin, zinc, alloys containing iron, alloys containing copper, alloys containing tin, or alloys containing zinc. Similar to the base polymer material, the filler material may be a virgin material or may have include an amount of recycled material.

The size and geometry of the inner layer 110 may control the characteristics of the blanket 100. As discussed above, the inner layer 110 may be a continuous sheet of material. In some examples, the inner layer 110 may generally extend the entire length and width of the blanket 100, or in other examples the inner layer 110 may extend at least 60 percent of the overall length and extend at least 60 percent of the overall width of the blanket 100. In still other examples, the inner layer 110 may comprise smaller continuous sheets that are less than 25 percent of the overall length and/or less than 25 percent of the overall width of the blanket 100. In addition, the thickness of the inner layer 110 may greatly affect the softness and feel of the blanket 100 as well as the weight. The thickness of the inner layer 110 may help to control the weight of the inner layer 110, such that the weight of the inner layer 110 may be approximately 5 pounds or within a range of 0.5 pounds and 10 pounds, but as an option, the inner layer 110 may be up to 60 pounds. As the thickness increases, the blanket 100 may feel stiffer because inner layer 110 may have a stiffness or flexural rigidity that is greater than the stiffness of the top and bottom layers 102, 104. The inner layer 110 may have a thickness of within a range of 0.005 inches and 0.10 inches, or may have a range of 0.003 inches and 0.20 inches, or may be within a range of 0.001 inches and 0.25 inches.

Figure 3:
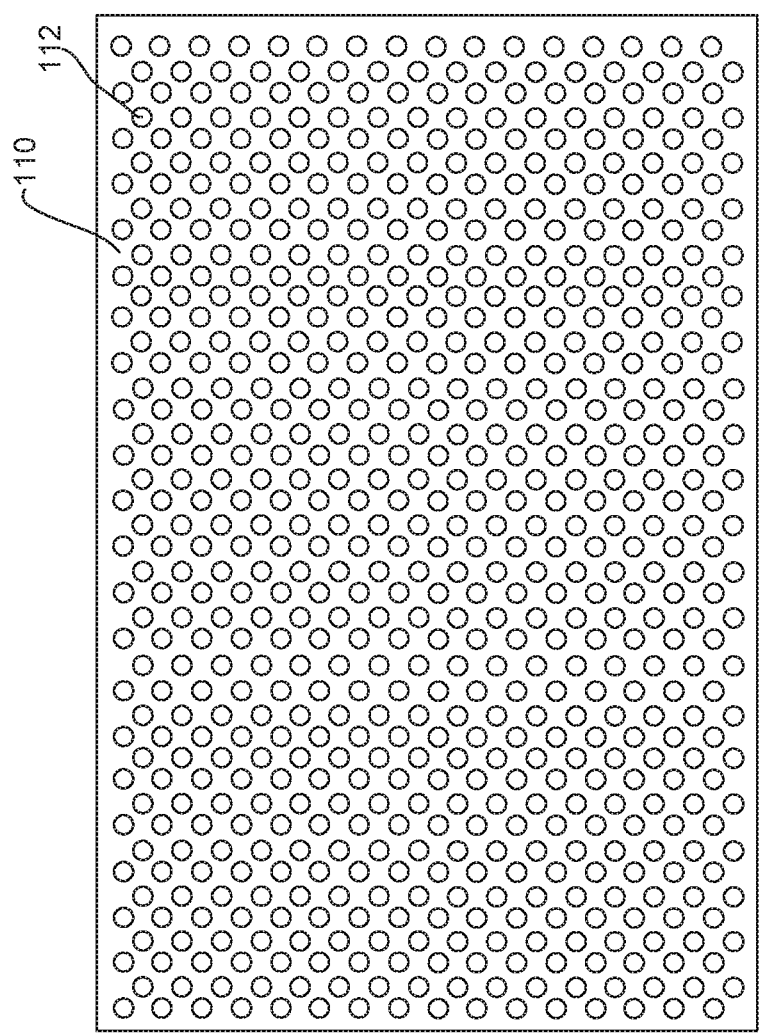
FIG. 3 is a top view of an inner layer of the weighted blanket of FIG. 1 as disclosed herein.

The inner layer 110 may have a plurality of ventilation apertures 112 that extend through the continuous sheet. These ventilation apertures 112 may help to provide ventilation through the blanket 100 to prevent the blanket 100 from holding too much heat, while also increasing the flexibility of the inner layer 110. The plurality of ventilation apertures 112 may extend through the entire thickness of the inner layer 110. Each ventilation aperture 112 may comprise a closed geometric shape, such as a circular shape, oval shape, elliptical shape, square, triangular, elongated slit, or other geometric similar shape. In addition, the size of each ventilation aperture 112 may be defined by the largest distance across each ventilation aperture 112. For example, the largest distance across each ventilation aperture 112 may be approximately 1.25 inches, or within a range of 0.75 inches and 2.0 inches, or within a range of 0.125 inches and 2.5 inches. For example, the plurality of ventilation apertures 112 may comprise at least one ventilation aperture with a circular shape or as shown in the embodiment of FIG. 3 all of the plurality of ventilation apertures 112 may have a circular shape. Each of these circular shaped ventilation apertures may have a diameter between 0.75 inches and 2.0 inches, or optionally have a diameter between 0.125 inches and 2.5 inches. As another option, the plurality of ventilation apertures 112 may have different shapes or sizes. For example, some of the ventilation apertures of the plurality of ventilation apertures 112 may have a first shape and some of the ventilation apertures of the plurality of ventilation apertures 112 may have a second shape different than the first shape. The different shaped ventilation apertures 112 may be arranged in a pattern, such as an alternating pattern, where the first shape may be next to or adjacent the second shape. As still another option, the different shaped ventilation apertures 112 may be grouped in different regions of the inner layer, such that the first shaped ventilation apertures 112 are located in a first region of the inner layer 110 and the second shaped ventilation apertures 112 are located in a second region of the inner layer 110. The plurality of ventilation apertures 112 may be uniformly spaced apart in a repeating or symmetrical pattern as shown in the embodiment illustrated in FIG. 3, or alternatively, the ventilation apertures may be non-uniformly spaced apart in a random or asymmetrical arrangement. The spacing between each ventilation aperture 112 may be at least half the maximum distance across each ventilation aperture, for example, if the ventilation apertures 112 are circularly shaped, the spacing between ventilation apertures 112 may be at least half of the diameter of the ventilation aperture 112. Alternatively, the spacing between the ventilation apertures 112 may be at least equal to the maximum distance across each ventilation aperture 112. As another option, the size and spacing of the plurality of ventilation apertures 112 may be defined as a percentage of the total area of the plurality of ventilation apertures 112 compared to the surface area of the inner layer 110, where the surface area of the inner layer 110 is defined by the product of the length and the width of the inner layer 110. For example, the area of the plurality of ventilation apertures 112 may comprise approximately 50 percent of the surface area of the inner layer 110, or the area of the plurality of ventilation apertures 112 may be within a range of 30 percent and 70 percent of the surface area of the inner layer 110.

As discussed above, the inner layer 110 may be formed from the core material where the core material is formed in large sheets, where the sheets may be formed up to 90 inches in width. These sheets of core material may be stamped, cut, or die cut to the desired shape depending on the desired size for each blanket 100. In addition, the plurality of ventilation apertures 112 may be stamped or cut out, using a variety of cutting methods such as CNC cutting, router cutting, laser cutting, water jet cutting, or die cutting, or other methods known to one skilled in the art.

The top layer 102 may be formed from a first fabric material, and the bottom layer 104 may be formed from a second fabric material. The top and bottom layers 102, 104 may be sheets of fabric without any openings (other than where the stitching 108, 109 may be present). The first fabric material may be the same material as the second fabric material, or the first fabric material may be a different material as the second fabric material. Additionally, the first fabric material and the second fabric material may be a continuous sheet of fabric or a plurality of fabrics stitched together, such as in a quilted manner, that form each of the top layer 102 and the bottom layer 104. For example, the first fabric material and the second fabric material may be formed from a natural fiber, a synthetic fiber, or a blends of fibers. These exemplary materials may include a cotton fiber, a polyester fiber, a polyamide fiber, a polypropylene material, a nylon material, a bamboo material, a hemp material, a felt material, a waterproof material, a vinyl material, waterproof/water resistant materials, EVA, a PVC material, a thermoplastic polyurethane material, a moisture-wicking material, an insulating material, or other suitable material.

As an alternate embodiment, the inner layer 110 may comprise multiple inner layers 110 as described herein. By using thin multiple inner layers 110, the weight of the blanket 100 may be increased without significantly reducing the flexibility of the blanket 100. The multiple inner layers 110 may not be joined to each other beyond the stitching 108 and/or the central stitching 109 to allow more freedom of movement, or optionally the multiple inner layers 110 may be joined to each other, or as another option a first inner layer 110 may be joined to a second inner layer 110, but neither the first inner layer 110 nor the second inner layer 110 may be joined to a third inner layer 110. In embodiments having multiple inner layers 110 joined together, the inner layers 110 may be attached to each other using adhesives, sonic welding, stitching, heat laminate welding, or mechanical means such as staples and rivets. By using multiple inner layers 110, each inner layer 110 may be made thinner such that a plurality of thinner inner layers 110 may be more flexible than a single thicker inner layer 110 while they both have the same weight.

As shown in the partial cross-sectional views of FIGS. 5-9, the blanket 100 may include multiple inner layers 110. Each layer 110 of the plurality of inner layers 110 may be identical in shape and size to the adjacent layer 110 where the adjacent inner layers 110 are arranged above or below each other, such the inner layers 110 contact each other.

Figure 4:
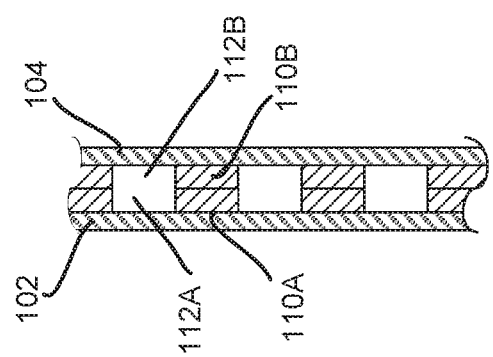
FIG. 4 is an enlarged partial cross-section view of an alternative embodiment of the weighted blanket of FIG. 1.

Alternatively, each layer 110 of the plurality of layers 110 may be different in size, thickness, core material density, size and/or shape of the ventilation apertures 112, or even the presence of the ventilation apertures 112. The plurality of inner layers 110 may be any number of inner layers 110, such as two layers 110 as shown in FIGS. 4, 7, 8, and 9, three layers 110, four layers 110 as shown in FIGS. 5 and 6, five layers 110, or even ten layers 110. In some embodiments, the plurality of ventilation apertures 112A on a first inner layer 110A may be substantially aligned with the plurality of ventilation apertures 112B of the adjacent inner layer 110B as illustrated in FIGS. 4 and 5. In addition, in the embodiment shown in FIG. 6, the multiple inner layers 110 may comprise at least one solid continuous sheet and at least one continuous sheet having a plurality of ventilation apertures 112. As another option, a first inner layer 110A of the multiple inner layers 110 may be arranged such that the ventilation apertures 112A are not aligned with the plurality of ventilation apertures 112B on the adjacent inner layer 110B as shown in the FIG. 7. FIG. 8 illustrates another embodiment where the inner layers 110 are solid continuous sheets without ventilation apertures, while FIG. 9 illustrates another exemplary embodiment where the top layer 102 comprises multiple layers 102 and the bottom layer 104 comprises multiple layers 104. By incorporating multiple fabric layers 102, 104 on top of one another the softness of the blanket 100 may be increased. In embodiments having multiple top or bottom layers 102, 104, the top and bottom layers 102, 104 may have any of the properties described above related to the top and bottom layers 102, 104.

For embodiment illustrated in FIG. 10, the features are referred to using similar reference numerals under the "2xx" series of reference numerals, rather than "1xx" as used in the embodiments of FIGS. 1-9. Accordingly, certain features of the blanket 200 that were already described above with respect to blanket 100 of FIGS. 1-9 may be described in lesser detail, or may not be described at all. FIGS. 10 and 11 illustrate an embodiment of blanket 200. Blanket 200 is similar to blanket 100 except the inner layer 210 may comprise a plurality of inner layers 210, where the inner layers 210 have a length and/or a width that is a portion of the entire length or the entire width of the blanket. The inner layers 210 may be continuous sheets formed from a core material and may have any of the properties of inner layer 110 described above. The inner layers 210 may be arranged in a substantially coplanar manner when the blanket 200 is lying on a flat surface, such that at least one of the perimeter edges 211 of the inner layer 210 may be arranged next to and/or spaced apart from nearest inner layer 210. As shown in FIGS. 10 and 11, the plurality of inner layers 210 may be arranged as multiple sheets that extend a portion of the overall length of the blanket 200 and/or also a portion of the overall width, such that perimeter edge 211A of inner layer 110A is spaced apart from the perimeter edge 211B of inner layer 210B. For example, the inner layers 210 may be arranged to have a perimeter edge 211A of a first inner layer 210A may be spaced a minimum distance of approximately 1 inch from a perimeter edge 211B of a second inner layer 210B nearest the first inner layer 210A, or in other embodiments the spacing may be within a range of 0.50 inches and 1.5 inches, or the spacing may be within a range of 0.25 inches and 2.0 inches. Having the inner layers spaced apart from each other may help improve the overall flexibility of the blanket to have it drape smoothly over the user. The blanket 200 may have additional stitching 208 to secure the positioning of the inner layers 210 relative the perimeter edges 206 of the blanket 200. As another option, the inner layers 210 may be a single layer or a plurality of inner layers 210 similar to the inner layers 110 described above in the embodiments of FIGS. 1-9.

FIGS. 12-13 illustrate an embodiment of blanket 300. The features of blanket 300 are referred to using similar reference numerals under the "3xx" series of reference numerals, rather than "1xx" as used in the embodiments of FIGS. 1-9. Accordingly, certain features of the blanket 300 that were already described above with respect to blanket 100 of FIGS. 1-9 may be described in lesser detail, or may not be described at all. Blanket 300 may have a plurality of inner layers 310 where each inner layer 310 has a length that is substantially equal to its width. Alternatively, the length may be greater than the width or the width may be greater than the length. The length of each inner layer 310 may be within a range of 2 percent and 30 percent of the overall length of the blanket 300, and the width may be within a range of 2 percent and 30 percent of the overall width of the blanket 300. As shown in FIG. 12, the inner layers 310 are arranged side by side, where the inner layers 310 may be arranged next to and/or spaced apart from one another to help increase the flexibility of the blanket 300. Similar to the embodiment of blanket 200, the inner layers 310 may be arranged to have a perimeter edge 311A of a first inner layer 310A spaced a minimum distance of approximately 1 inch from a perimeter edge 311B of a second inner layer 310B located nearest the first inner layer 310A, or in other embodiments the spacing may be within a range of 0.50 inches and 1.5 inches, or the spacing may be within a range of 0.25 inches and 2.0 inches. The blanket 300 may have additional stitching 308 to secure the positioning of the inner layers 310 relative the perimeter edges 306 of the blanket 300. In some embodiments, the perimeter edge 311A may be substantially parallel to the perimeter edge 311B. The inner layers 310 may be continuous sheets formed from a core material and may have any of the properties of inner layer 110 described above. As another option, the inner layers 310 may be a single layer or a plurality of inner layers 310 similar to the inner layers 110 described above in the embodiments of FIGS. 1-9.

In addition, the weight of each of the inner layers 310 may be substantially the same to keep the blanket evenly weighted. Alternatively, the weight of the inner layers 310 may be different to bias the center of gravity of the blanket 300 towards one of the perimeter edges 306. Each of the inner layers 310 may be positioned within a pocket arranged within one of the top and/or bottom layers 102, 104 to secure the inner layers 310 to the blanket 300. In some embodiments, the blanket 300 may have additional stitching to secure the positioning of the inner layers 310 relative the perimeter edges 306 of the blanket 300.

While various embodiments have been described, it will be apparent to those of ordinary skill in the art that many more embodiments and implementations are possible that are within the scope of the claims. The various dimensions described above are merely exemplary and may be changed as necessary. Accordingly, it will be apparent to those of ordinary skill in the art that many more embodiments and implementations are possible that are within the scope of the claims. Therefore, the embodiments described are only provided to aid in understanding the claims and do not limit the scope of the claims.

We claim:

1. A blanket comprising:
   a top layer comprising a sheet of a first fabric material,
   a bottom layer comprising a sheet of a second fabric material,
   an inner layer positioned between the top layer and the bottom layer, wherein the inner layer is a continuous sheet of a core material, wherein the core material includes a base polymer material and a filler material, wherein the core material has a density between 0.6 grams per cubic centimeter and 10 grams per cubic centimeter, and
   wherein the top layer, the bottom layer, and the inner layer are joined together using a central stitch located in a central region of the blanket, wherein the central region is defined as an area spaced a distance from a perimeter edge of the blanket of at least thirty percent of a total width of the blanket.

2. The blanket of claim 1, wherein the inner layer has a thickness between 0.001 inches and 0.25 inches.

3. The blanket of claim 1, wherein the continuous sheet of the core material has a length that is at least 60 percent of a total length of the blanket.

4. The blanket of claim 1, wherein the base polymer material is one of a group consisting of: an ethylene vinyl acetate, a thermoplastic elastomer, a thermoplastic olefin, a thermoplastic vulcanizate, a styrenic block copolymer, a styrene ethylene butylene styrene, a thermoplastic rubber, a polyvinyl chloride, a polyurethane, a polyethylene, a polyethylene terephthalate, a polypropylene, a polyolefin, a thermoplastic, a foam, a thermoset plastic, a cured rubber, a silicone, a functionalized polymer, and a thermoplastic blend.

5. The blanket of claim 1, wherein the filler material is one of a group consisting of: a mineral, a sulfate, an oxide, a hydroxide, a sulfide, a carbonate, a phosphate, a halide, a silicate, a glass, diametric earth, a fabric material, or a different polymer with a higher density than the base polymer material, or other non-metallic material.

6. The blanket of claim 1, wherein the base polymer material is of one of a first group consisting of: a thermoplastic elastomer, a styrenic block copolymer, a styrene ethylene butylene styrene, and a thermoplastic rubber, and wherein the filler material is one of a second group consisting of: a sulfate, a fabric material, or a different polymer with a higher density than the base polymer material.

7. The blanket of claim 1, wherein the filler material is a metallic material.

8. The blanket of claim 1, wherein the filler material is non-toxic.

9. The blanket of claim 1, wherein the density of the core material is between 1.8 grams per cubic centimeter and 3.2 grams per cubic centimeter.

10. The blanket of claim 1, wherein the inner layer has a plurality of ventilation apertures extending through the inner layer.

11. The blanket of claim 10, wherein at least one ventilation aperture of the plurality of ventilation apertures has a circular shape.

12. The blanket of claim 10, wherein a largest distance across each ventilation aperture of the plurality of ventilation apertures is between 0.125 inches and 2.5 inches.

13. The blanket of claim 1, wherein the core material has a durometer between 1 Shore A and 87 Shore A, when measured per ASTM D2240.

14. The blanket of claim 1, wherein the inner layer comprises a plurality of inner layers, wherein a first inner layer of the plurality of inner layers is positioned adjacent and above a second inner layer of the plurality of inner layers.

15. A blanket comprising:
    a top layer comprising a sheet of a first fabric material,
    a bottom layer comprising a sheet of a second fabric material, and
    a plurality of inner layers positioned between the top layer and the bottom layer, wherein each inner layer of the plurality of inner layers is a continuous sheet of a core material, wherein the core material includes a base polymer material and a filler material, wherein the filler material has a higher density than the base polymer material, and
    wherein a first inner layer of the plurality of inner layers is spaced apart from and arranged next to a second inner layer of the plurality of inner layers, wherein a first perimeter edge of the first inner layer is spaced a minimum distance from a first perimeter edge of the second inner layer of the plurality of inner layers such that the minimum distance between the first perimeter edge of the first inner layer and the first perimeter edge of the second inner layer is within a range of 0.25 inches and 2 inches.

16. The blanket of claim 15, wherein at least one of the inner layers of the plurality of inner layers has a plurality of ventilation apertures.

17. The blanket of claim 16, wherein a largest distance across each ventilation aperture of the plurality of ventilation apertures is between 0.125 inches and 2.5 inches.

18. A blanket comprising:
    a top layer comprising a first fabric material,
    a bottom layer comprising a second fabric material, and
    an inner layer positioned between the top layer and the bottom layer, wherein the inner layer is a continuous sheet of a core material, wherein the core material includes a base polymer material and a filler material, and wherein the filler material has a density that is greater than a density of the base polymer material such that a density of the core material is within a range of between 0.6 grams per cubic centimeter and 10 grams per cubic centimeter, and wherein the inner layer has a plurality of ventilation apertures extending through the inner layer.

19. The blanket of claim 18, wherein at least one ventilation aperture of the plurality of ventilation apertures has a circular shape.

20. The blanket of claim 19, wherein the at least one circular shaped ventilation aperture has a diameter between 0.125 inch and 2.5 inches.

\* \* \* \* \*